United States Patent [19]

Seguin et al.

[11] Patent Number: 5,085,870
[45] Date of Patent: Feb. 4, 1992

[54] SILANOL-BASED PRODUCT FOR CARE OF THE SUPERFICIAL LYMPHATIC VESSELS

[76] Inventors: Marie-Christine Seguin; Jean Gueyne, both of Perigord 1, 6 Lacets Saint-Leon, Monte Carlo, Monaco

[21] Appl. No.: 577,794

[22] Filed: Sep. 5, 1990

Related U.S. Application Data

[63] Continuation of Ser. No. 241,601, Sep. 8, 1988, abandoned.

[30] Foreign Application Priority Data

Sep. 9, 1987 [FR] France ................. 87 12480

[51] Int. Cl.5 ............... A61K 31/225; A61K 35/78; A61K 33/00; A61K 37/00
[52] U.S. Cl. .................. 424/547; 424/195.1; 424/602; 514/2; 514/63
[58] Field of Search .............. 424/195.1, 547, 600, 424/602; 514/2, 21, 63

[56] References Cited

U.S. PATENT DOCUMENTS

| | | | |
|---|---|---|---|
| 3,946,108 | 3/1976 | Tomlinson et al. | 424/49 |
| 4,020,154 | 4/1977 | Perla et al. | 424/49 |
| 4,393,045 | 7/1983 | Henderson et al. | 424/547 |
| 4,795,638 | 1/1989 | Ayache et al. | 424/195.1 |

FOREIGN PATENT DOCUMENTS 1234213 10/1960 France .

Primary Examiner—John W. Rollins
Attorney, Agent, or Firm—Ostrolenk, Faber, Gerb & Soffen

[57] ABSTRACT

Aqueous composition for care of the superficial lymphatic vessels, containing one or more silanols or silanol derivatives in conjunction with concholytic acid.

13 Claims, No Drawings

SILANOL-BASED PRODUCT FOR CARE OF THE SUPERFICIAL LYMPHATIC VESSELS

This is a continuation of application Ser. No. 07/241,601 filed on Sept. 8, 1988, now abandoned.

The present invention relates to a product for care of the superficial lymphatic vessels. It comprises in particular a gel or an emulsion intended for massaging parts of the body when it is desired to treat the lymphatic vessels.

The importance of the lymphatic system is often considerably neglected and the pharmacopea is poor in compositions capable of improving the state of the lymphatic vessels. However, these vessels are subject to various injuries and disorders which require treatment, so as to avoid dermatological or even general complications of the individual. Thus alterations in the lymphatic wall and a fall in its resistance, obstruction of the capillaries, thickening of the lymph, formation of cytotoxic malonaldehyde and other anomalies have to be combatted. The present-day pharmacopea in its dermatological section is concerned virtually solely with veins and circulatary capillaries, without providing specific medicaments for the lymphatic system. This situation is without disadvantage when products proposed for disorders of the venous function are also efficacious against the lymphatic ducts; thus for example, creams or ointments based on aescine, melilot extract and/or sterolic heterosides of ruscus aculeatus are generally suitable both in the case of venous insufficiency and of the lymphatic vessels; but this is not the case for numerous other known medicaments.

On the other hand, products are not known which are capable at the same time of regenerating the lymphatic wall, regulating the viscosity of the lymph and exerting an anti-oedematous action. It is known that engorgement of the lymphatic ducts, the function of which is the elimination of large molecules, toxins, bacteria, lipids, peptides, etc., causes oedema of the adjacent tissues and a certain degree of cytotoxicity. To remedy these disadvantages, various physical means have been utilised, particularly manual lymphatic drainage or sequential pressotherapy; however, in the absence of a biochemical agent capable of use in conjunction with these procedures, the results leave much to be desired.

The present invention fills this gap in the prior art: it provides a composition intended specifically for care of the lymphatic vessels, capable of acting simultaneously on several of the conditions mentioned above. Thus independently of the venous state of the patient and thus contrary to what has been carried out up to the present, the new product according to the invention can improve the texture of the lymphatic wall and increase the resistance of the corresponding capillaries, while restoring the viscosity of the lymph to an appropriate level and acting on the microsphincters for relaxing them, thus producing an anti-oedematous action.

These new and important results are obtained according to the invention by the association of certain natural active products with one or more silanols which, in conjunction with their own specific action, reinforce that of the natural products or even induce in them new properties.

According to a first aspect of the invention, the new composition for care of the lymphatic vessels is characterised in that it contains one or more silanols or silanol derivatives accompanied by concholytic acid. For cutaneous applications, this composition is made up in the form of an aqueous gel, emulsion or aqueous ointment, according to the known technique, which consequently is not described here.

The preferred contents of silanols and/or their derivatives are in the region of 0.05 to 0.5% by weight, the proportions of concholytic acid being of the same order.

Particularly suitable silanols for carrying out the invention are of the type $R_n\text{-Si(OH)}_{(4-n)}$ where R is a hydrocarbon radical, particularly $C_1$ to $C_{18}$ alkyl, n is 1 to 3, where all or part of the H's can be replaced by a $C_1$ to $C_{18}$ alkyl. In the most usual silanols, R is a $C_1$ to $C_4$ alkyl. Compounds are designated above by the term "silanol derivatives" in which a silanol is combined with another molecule, in particular an acid. Such derivatives known in the art have been described for example in French Patent Number 1 234 213 which gives several formulae on page 2. In these compounds $$R_n\text{Si(OH)}_{(4-n)}.X.R'\text{COOH} \qquad (1)$$

R and n have the same significance as above, X in general is of the same order as the number of OH attached to Si, namely (4-n), when any H of these oxydriles has not been replaced by a hydrocarbon group. As to the acid R'COOH, various pharmaceutically-acceptable organic acids can be used, such as the amino acids. In a non-limitative manner, reference can be made to acetic, sebacic, citric, tartric, lactic, nicotinic, ascorbic, folic, salicylic, acetylsalicylic, lactic, hyaluronic, aspartic and glutamic acids, glycine, serine, threonin, tyrosine, etc.

Silanol derivatives which can also be employed include siloxanes, for example of the type

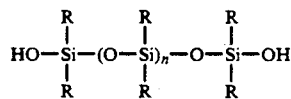

where R is a hydrocarbon group and n is a number from 0 to 20, but preferably from 0 to 4.

As regards concholytic acid, because its especially practical source is the shells of molluscs and particularly mother-of-pearl, it is advantageously used in the form of a mother-of-pearl extract. This aqueous extract results from the controlled acid hydrolysis of mother-of-pearl.

In a particular embodiment of the invention, the composition also contains one or more "proteosilanes", that is combinations of organic compounds of silicon with protides. The conjoint action of silanols and proteosilanes is thus reinforced and localised on the superficial lymphatics. Proteosilanes can be represented diagrammatically by the formula

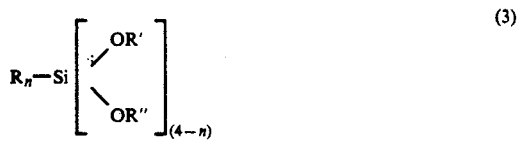

where R is an organic group, in particular $C_1$ to $C_{18}$ alkyl or alkenyl, n=1 to 3, R' is a group active on the skin, for example theophylline, theophyllineacetic or glycyrrhizic acid, acetyl-tyrosine acid, etc., and R" is a protide, lipoprotide or nucleoprotide group, in particular a peptide, polypeptide or cyclopeptide particularly albumin, fibrin, collagen, keratin, elastine or other proteinic groups.

For the compositions according to the invention derivatives of silicon according to the formula (3) are particularly suitable in which R is CH₃, n=1 or 2, R' is one of the acid groups mentioned and R" is elastine solubilised by partial hydrolysis.

According to another feature of the invention, the composition preferably contains an essential oil, particularly a terpene oil, for example oil of lavender. Such oils modify the viscosity and quality of the lymph due to the presence of silanols which favour their penetration and incorporation into the lymphatic liquid. The proportion of oil is preferably from 0.05 to 2% by weight.

As the role of glycosides, particularly rutosides or saponosides, is known for increasing the resistance of the capillaries, these substances when they are present in the composition according to the invention promote an activation by the silanol of their normalising action on the texture of the lymphatic wall. Such substances are for example polyphenols in the cases of extracts of Piloselle, Centella asiatica or Arnica, this normalisation causing a reduction in oedemas; or, they are extract of Ruscus, with—as a second effect—an increase in the lymphatic capillary resistance. Thus in a variant of the invention, the composition contains one or more glycosides of this type, for example rutine, ruscus extract, hydroxyethylrutoside or the like. Additives favouring normalisation of the texture of the lymphatic wall are extracts of piloselle, centella asiatica and/or arnica.

The relaxant action on microsphincters which is accompanied by an anti-oedematous action of the composition according to the invention can be reinforced by the addition of natural extracts, such as for example those of ginkgo and/or melilot. The proportions of the natural extracts in the composition preferably range between about 0.05 and 2% by weight.

A gel or an emulsion containing silanol and concholytic acid applied topically has the interesting advantage of exerting a localised action on the superficial lymphatic vessels, normalising the texture of their wall, regulating the viscosity of the lymph and exerting an anti-oedematous action. The effects are more apparent than when only one of the two constituents in question is applied. The action can be more intense and more complete when certain extracts of plants are added to these constituents, such as proteosilanes and terpene derivatives. The regeneration of collagen and elastine fibres and the restructuring of proteoglucanes, due to the silanol, are accompanied by an intervention in the metabolism of fatty bodies; thus during lipolysis, the silanol favours the formation of unsaturated fatty acids and protects them from cytotoxic peroxydation, capable of raising the viscosity of the lymph. On the other hand, the reduction of oedemas by modification of the capillary permeability under the effect of the silanol is considerably potentialised by the concholytic acid.

The invention is illustrated by the non-limitative examples which follow.

EXAMPLE 1

In a gel formed from 100 ml of water containing 1 g of the water-soluble carboxypolymethylene resin known under the name "CARBOPOL", 0.1 g of concholytic acid taken in the state of its extract of mother-of-pearl is dispersed, together with 0.04 g of dimethylsilanol dilactate

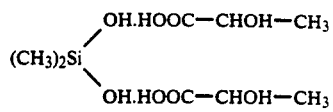

and 0.06 g of methyl-silane-triol hyaluronate.

These two derivatives of silanol have been employed in the form of 1% aqueous solutions. Also 0.1 g of oil of lavender is dispersed in the gel.

The composition obtained has proved to be very efficacious for the regeneration and reinforcement of the lymphatic vessels and reduction i viscosity of the lymph during its application with massaging.

EXAMPLE 2

0.5 g of the proteosilane according to the formula given above, in which R=CH₃, n=1, R' is the theophyllin-acetic acid group and R" is solubilised elastine, is incorporated in 100 ml of the gel of Example 1. Application of the composition gives the same good results as that of Example 1 with, in addition, a localised improvement in the superficial lymphatic vessels.

EXAMPLE 3

The gel of Example 2 was combined with 1 g of ruscus extract which contributes to increasing the resistance of the lymphatic capillaries.

EXAMPLE 4

1 g of melilot extract was dispersed in 100 ml of the gel of Example 3, to ensure good flow of the lymphatic material by its relaxant action on the microsphincters.

EXAMPLE 5

2 g of ginkgo extract, which perfects regulation of the lymphatic rate, with reduction of oedema, was dispersed in 100 ml of the gel according to Example 3.

EXAMPLE 6

The gel according to Example 3 includes 1 g of piloselle extract for better regulation of the lymph flux.

EXAMPLE 7

The gel of Example 4 was combined with 0.1 g of hydrumine of arnica per 100 ml of gel, the favourable action of which on the lymphatic wall is potentialised by the presence of the silanol.

EXAMPLE 8

To the gel of Example 4 is added per 100 ml 0.1 g of a hydrumine of asiatic centelle; the effect is similar to that of the arnica in Example 7.

EXAMPLE 9

In Example 1, the oil of lavender is replaced with terebenthine.

EXAMPLE 10

In 100 ml of the aqueous gel formed from 100 ml of water containing in solution 2 g of polyvinylpyrrolidone, there are dispersed the following quantities in g of the constituents:

| | |
|---|---|
| oil of lavender | 0.1 |
| cohcholytic acid | 0.1 |
| hydroglycolic extract of arnica enriched with the sterols of the plant | 0.1 |
| hydroglycolic extract of arnica enriched with the sterols of asiatic centelle | 0.1 |
| methyl-silane-triol lactate | 0.04 |
| methyl-silane-triol hyaluronate | 0.06 |
| Proteosilane E | 0.1 |
| Extract of melilot | 0.1 |
| Extract of ruscus | 0.1 |
| Extract of gingko | 0.2 |
| Extract of piloselle | 0.1 |

For this preparation, the Si compounds were each used in the form of a 1% aqueous solution. "Proteosilane E" designates the complex according to formula (3) in which R=C₂H₅, n=2, R' is an acetyl-tyrosine acid group and R" is solubilised structured elastine.

Applied with massage, this composition produces all the favourable effects indicated at the beginning of the present description.

EXAMPLE 11

In 100 ml of water 1 g of a non-ionic surfactant agent, sold under the mark "TWEEN 20" (polyoxyethylene monolaurate of sorbitan), is dissolved and 3 g of soft almond oil was emulsified with the solution obtained. Then in the emulsion so formed, the same constituents as in Example 10 were dispersed in the same proportions and in the same manner. Excellent results are obtained, as with the gel of Example 10.

We claim:

1. Aqueous composition for care for the superficial lymphatic vessels, comprising water containing 0.05 to 0.5% by weight of an aqueous extract of mollusk shells and 0.05 to 0.5% by weight of silanol derivative of the formula

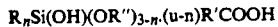

where R is $C_1$ to $C_{18}$ alkyl, R'COOH is a pharmaceutically acceptable acid, each R" is individually H or $C_1$ to $C_{18}$ alkyl, n is 1 to 3.

2. Composition according to claim 1, which said pharmaceutically acceptable acid R'COOH is selected from the group consisting of acetic acid, sebacic acid, citric acid, tartaric acid, lactic acid, nicotinic acid, ascorbic acid, folic acid, salicylic acid, acetyl salicylic acid hyaluronic acid, aspartic acid, glutamic acid, glycine, serine, threonine and tyrosine.

3. Composition according to claim 2, which additionally contains about 0.05 to about 2% by weight of at least one extract of the plants; *Arnica montana, Melilotus officinalis, Ruscus aculeatus, Ginkgo biloba* and *Hieracium pilosella*.

4. Composition according to claim 1, which contains an amount of water-soluble resin sufficient to form a gel.

5. The composition according to claim 1, which contains 0.05 to 0.5% by weight of a proteosilane of the formula

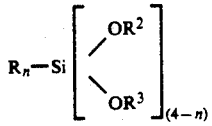

where R is a $C_1$ to $C_{18}$ alkyl, n is 1 to 3, $R^2$ is a moiety of theophylline, theophylline-acetic acid, glycyrrhizic acid or acetyl tyrosine acid, and $R^3$ is a moiety of a peptide, polypeptide, cyclopeptide or protein.

6. Composition according to claim 5, wherein $R^3$ is a moiety of albumin, fibrin, collagen, keratin or elastine.

7. Composition according to claim 6, which contains an amount of water-soluble resin sufficient to form a gel.

8. Composition according to claim 7, wherein said water soluble resin is carboxypolymethylene or poylvinyl pyrrolidone.

9. Composition according to claim 6, which additionally contains about 0.05 to about 2% by weight of at least one extract of the plants: *Arnica montana, Melilotus, officinalis, Ruscus aculeatus, Ginkgo biloba* and *Hieracium pilosella*.

10. Composition according to claim 9, wherein the silanol derivative comprises methyl silane triol lactate and methyl silane triol hyaluronate, and in the proteosilane R is $C_2H_5$, n is 2, $R^2$ is an acetyl tyrosine acid moiety, and $R^3$ is a solubilized elastine moiety.

11. Composition according to claim 1, wherein the silanol derivative comprises methyl silane triol lactate and methyl silane triol hyaluronate.

12. Composition according to claim 1, which additionally contains about 0.05 to 2% by weight of at least one extract of the plants; *Arnica montana, Melilotus officinalis, Ruscus aculeatus, Ginkgo biloba* and *Hieracium pilosella*.

13. Composition according to claim 2, wherein the silanol derivative comprises methyl silane triol lactate and methyl silane triol hyaluronate.

* * * * *